(12) United States Patent  
Slagle

(10) Patent No.: US 9,759,244 B2  
(45) Date of Patent: Sep. 12, 2017

(54) ORTHOPAEDIC TOOL CLUSTER CLAMP AND ORTHOPAEDIC TOOLS

(71) Applicant: Biomet Manufacturing, LLC, Warsaw, IN (US)

(72) Inventor: Paul Slagle, Leesburg, IN (US)

(73) Assignee: Biomet Manufacturing, LLC, Warsaw, IN (US)

(*) Notice: Subject to any disclaimer, the term of this patent is extended or adjusted under 35 U.S.C. 154(b) by 159 days.

(21) Appl. No.: 14/732,299

(22) Filed: Jun. 5, 2015

(65) Prior Publication Data

US 2015/0351779 A1  Dec. 10, 2015

Related U.S. Application Data

(60) Provisional application No. 62/008,669, filed on Jun. 6, 2014, provisional application No. 62/008,682, filed on Jun. 6, 2014, provisional application No. 62/008,656, filed on Jun. 6, 2014.

(51) Int. Cl.

| | |
|---|---|
| F16B 2/12 | (2006.01) |
| A61G 13/10 | (2006.01) |
| A61B 17/17 | (2006.01) |
| A61B 17/16 | (2006.01) |
| A61B 90/57 | (2016.01) |
| A61B 90/50 | (2016.01) |
| F16B 2/18 | (2006.01) |

(52) U.S. Cl.
CPC ............ *F16B 2/12* (2013.01); *A61B 17/1644* (2013.01); *A61B 17/17* (2013.01); *A61B 90/50* (2016.02); *A61B 90/57* (2016.02); *A61G 13/101* (2013.01); *A61B 2017/1651* (2013.01); *F16B 2/185* (2013.01); *Y10T 74/18984* (2015.01)

(58) Field of Classification Search
CPC . A61G 13/101; Y10T 74/18984; A61B 90/50; A61B 90/57; A61B 17/1644; A61B 17/17; A61B 2017/1651; F16B 2/12; F16B 2/185
USPC ....................................................... 211/85.13
See application file for complete search history.

(56) References Cited

U.S. PATENT DOCUMENTS

| | | | | |
|---|---|---|---|---|
| 1,509,022 A | * | 9/1924 | Noble .................. | E21B 15/006 24/285 |
| 1,667,669 A | * | 4/1928 | Megee ..................... | A47F 5/04 211/24 |
| 5,294,006 A | * | 3/1994 | Deschino .............. | A47F 5/0853 211/103 |

(Continued)

*Primary Examiner* — Ko Hung Chan  
*Assistant Examiner* — Korie H Chan  
(74) *Attorney, Agent, or Firm* — Schwegman Lundberg & Woessner, P.A.

(57) ABSTRACT

An orthopaedic tool cluster clamp includes a pair of jaws held together and defining a distance therebetween, the jaws being movable relative to one another to adjust the distance; a connector holding the jaws together, with actuation of the connector adjusting the distance between the jaws; a cam base including a ramped portion statically associated with one of the jaws; and a cam lever pivotally connected to the connector about an axis of rotation and held against the cam base. The cam lever defines a profile such that rotating the cam lever along the ramped portion and pivoting the cam lever about the axis of rotation both cause actuation of the connector.

18 Claims, 17 Drawing Sheets

(56) References Cited

U.S. PATENT DOCUMENTS

| | | | | |
|---|---|---|---|---|
| 6,301,749 | B1 * | 10/2001 | Chen | B62K 3/002 |
| | | | | 16/427 |
| 6,494,327 | B2 * | 12/2002 | Huang | A47F 5/0892 |
| | | | | 211/107 |
| 6,983,853 | B1 * | 1/2006 | Fickett | A47F 5/04 |
| | | | | 211/18 |
| 8,403,282 | B2 * | 3/2013 | Aguirrezabal | B62K 23/06 |
| | | | | 211/17 |
| 8,528,748 | B2 * | 9/2013 | Shaha | B62H 3/12 |
| | | | | 211/17 |
| 8,820,543 | B2 * | 9/2014 | Huang | B62H 3/12 |
| | | | | 211/107 |
| 9,090,306 | B2 * | 7/2015 | Wang | B62K 15/008 |
| 9,145,181 | B2 * | 9/2015 | Peruzzo | A47F 5/08 |

* cited by examiner

ORTHOPAEDIC TOOL CLUSTER CLAMP AND ORTHOPAEDIC TOOLS

CROSS REFERENCE TO RELATED APPLICATIONS

This is a non-provisional application based upon U.S. provisional patent application Ser. No. 62/008,656 entitled "LEUR LOCK", filed Jun. 6, 2014, U.S. provisional patent application Ser. No. 62/008,669, entitled "CLUSTER CLAMP", filed Jun. 6, 2014, and U.S. provisional patent application Ser. No. 62/008,682, entitled "MULTITOOL", filed Jun. 6, 2014, which are all incorporated herein by reference.

BACKGROUND OF THE INVENTION

1. Field of the Invention

The present invention relates to surgical devices, and, more particularly, to orthopaedic cluster clamps.

2. Description of the Related Art

During an orthopaedic surgical procedure, several devices might need to be held in a line for a surgeon to use during the procedure. Some of these devices might include pins and drill guides. As is known, orthopaedic pins and drill guides can be circular in shape and typically have significantly different diameters.

To hold pins and drill guides during the procedure, one or more tool cluster clamps can be used to hold the pins and/or drill guides in a line. Due to the size difference between the pins and drill guides, the tool cluster clamps can be formed to have differently sized tool holders, some of which are sized to hold a pin and some of which are sized to hold a drill guide. This is inconvenient for the surgeon, because the placement of the pin(s) and/or drill guide(s) in the tool cluster clamp must be based on the location of the pin holders and the drill guide holders in the tool cluster clamp, rather than the surgeon's preference.

What is needed in the art is an orthopaedic tool cluster clamp that allows for more flexibility in the placement of various tools within the tool cluster clamp.

SUMMARY OF THE INVENTION

The present invention provides an orthopaedic tool cluster clamp with a cam assembly that allows for four or more different clamping positions through rotation and pivoting of a cam lever.

The invention in one form is directed to an orthopaedic tool cluster clamp including: a pair of jaws held together and defining a distance therebetween, the jaws being movable relative to one another to adjust the distance; a connector holding the jaws together, with actuation of the connector adjusting the distance between the jaws; a cam base including a ramped portion statically associated with one of the jaws; and a cam lever pivotally connected to the connector about an axis of rotation and held against the cam base. The cam lever defines a profile such that rotating the cam lever along the ramped portion and pivoting the cam lever about the axis of rotation both cause actuation of the connector.

The invention in another form is directed to a cam assembly including: a cam base having a ramped portion; and a cam lever held against the cam base and having a connection feature defining an axis of rotation. The cam lever defines a profile such that rotating the cam lever along the ramped portion and pivoting the cam lever about the axis of rotation both cause linear movement of the connection feature.

An advantage of the present invention is that the jaws of the tool cluster clamp can be adjusted to many different positions to clamp tools with varying sizes.

Another advantage is the distance between the jaws can be varied without using any special tools.

BRIEF DESCRIPTION OF THE DRAWINGS

The above-mentioned and other features and advantages of this invention, and the manner of attaining them, will become more apparent and the invention will be better understood by reference to the following description of embodiments of the invention taken in conjunction with the accompanying drawings, wherein.

Corresponding reference characters indicate corresponding parts throughout the several views. The exemplifications set out herein illustrate embodiments of the invention and such exemplifications are not to be construed as limiting the scope of the invention in any manner.

DETAILED DESCRIPTION OF THE INVENTION

Figure 1:
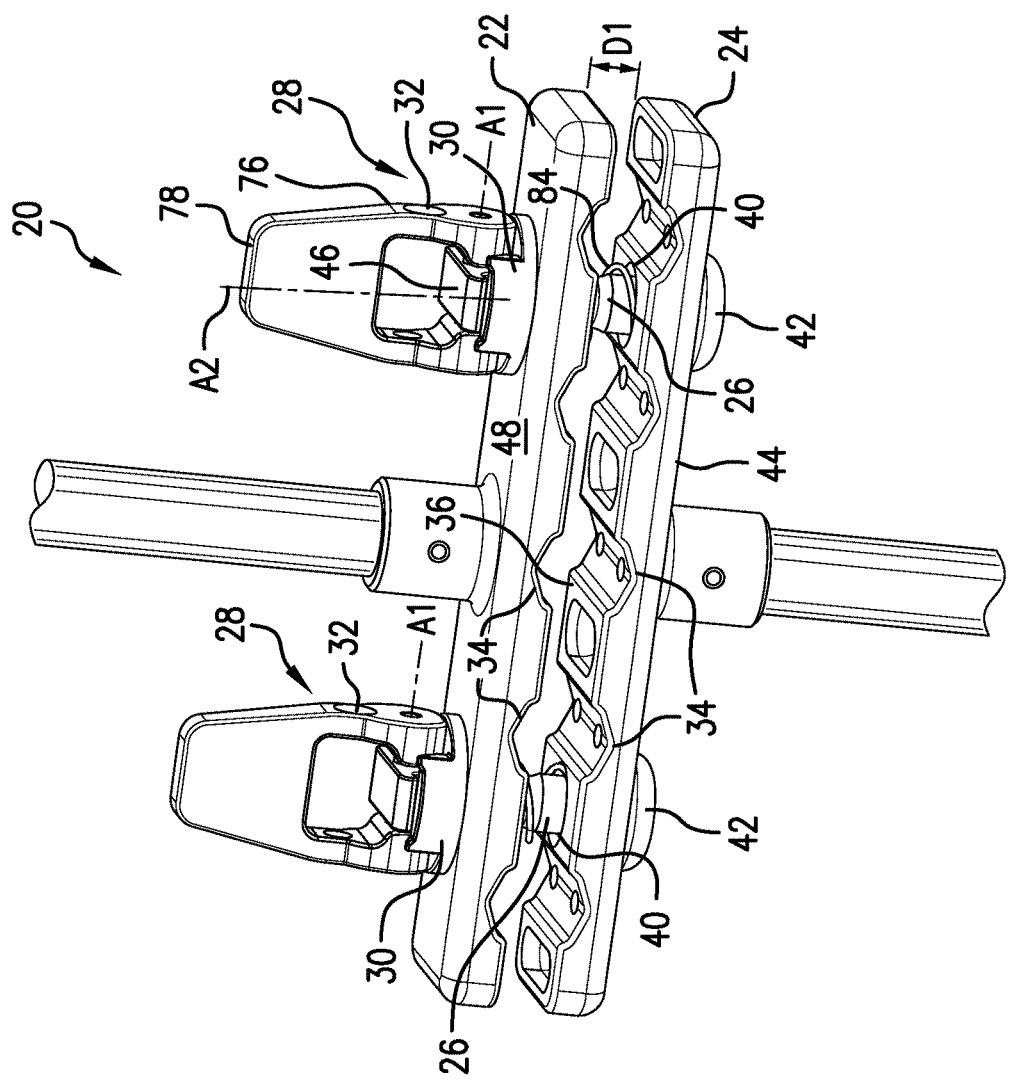
FIG. 1 is a perspective view of an embodiment of an orthopaedic tool cluster clamp according to the present invention.

Referring now to the drawings, and more particularly to FIGS. 1-6, there is shown an orthopaedic tool cluster clamp 20 which generally includes a pair of jaws 22 and 24 defining a distance D1 therebetween and held together by a pair of connectors 26, and a pair of cam assemblies 28 each including a cam base 30 statically associated with the jaw 22 and a cam lever 32 pivotally connected to the connector 26 about an axis of rotation A1. While two connectors 26 and cam assemblies 28 are shown as being included with the tool cluster clamp 20, the tool cluster clamp 20 can include only one connector 26 and cam assembly 28 and only one of such connectors 26 and cam assemblies 28 is described further herein for ease of description. As used herein, the jaws 22 and 24 are "held together" in the sense that they are not free to separate from one another, due to the connector 26, not that the jaws 22 and 24 have interior surfaces 36 that are necessarily pressed together. As can be seen, each of the jaws 22 and 24 includes holding recesses 34 formed on the interior surfaces 36 of the jaws 22 and 24 that are shaped to accept an orthopaedic tool, such as a drill sleeve 300 (shown in FIG. 3) or an orthopaedic pin 38 (shown in FIG. 6). The jaws 22 and 24 are movable relative to one another such that the distance D1 between the jaws 22 and 24 can be adjusted. The connector 26, which is held in connector openings 40 formed through each of the jaws 22 and 24, has an abutting portion 42 pressed against an exterior surface 44 of the jaw 24 and a ledged portion 46 pressed against the cam base 30, which is pressed against an exterior surface 48 of the jaw 22. In this sense, actuation of the connector 26, i.e., linear movement of the connector 26, relative to one of the jaws 22 or 24 causes the jaws 22 and 24 to move relative to one another and adjusts the distance D1 between the jaws 22 and 24.

Figure 2:
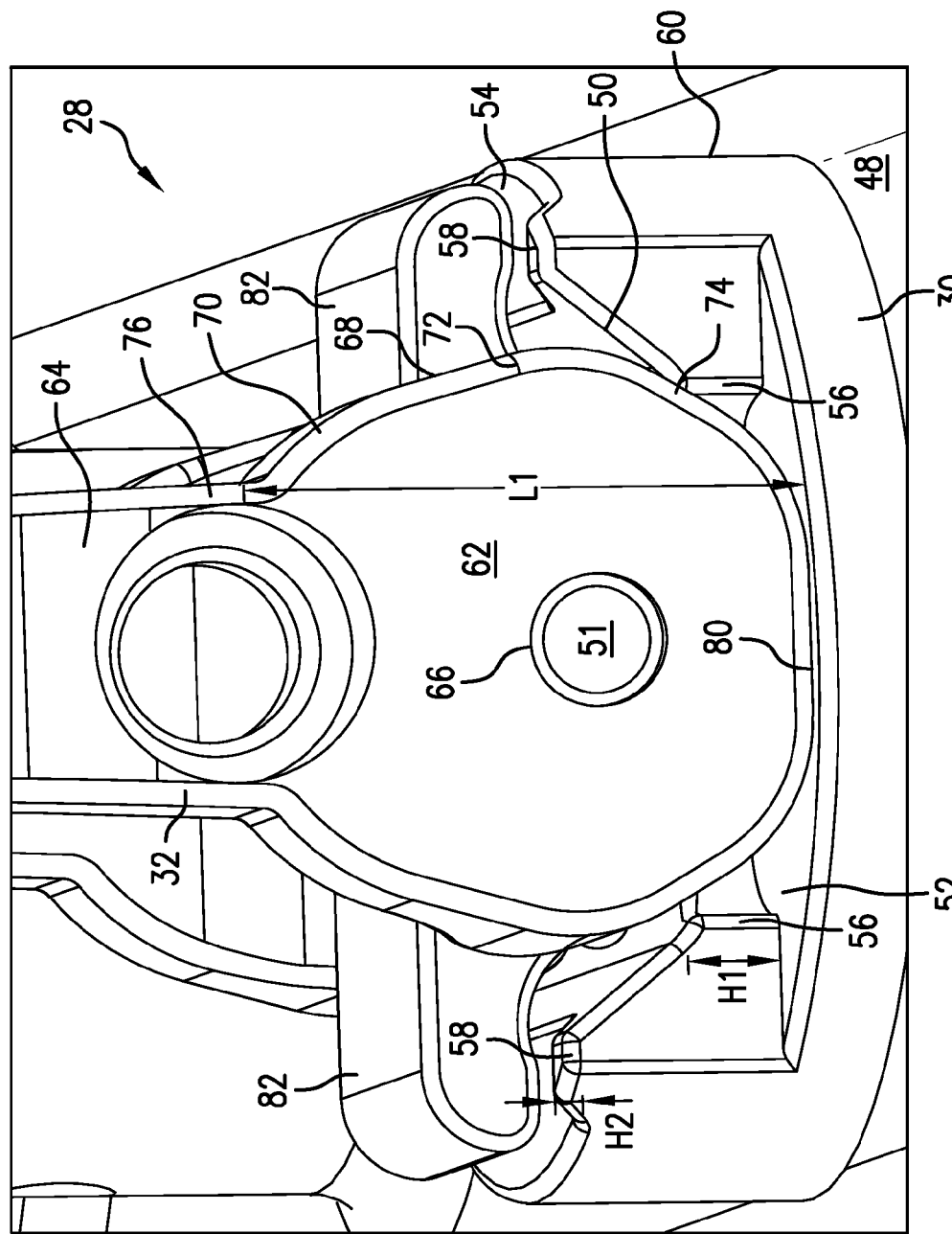
FIG. 2 is a perspective view of a cam assembly included on the tool cluster clamp shown in FIG. 1 in a first position.

Referring now specifically to FIG. 2, a close-up view of a portion of the cam assembly 28 is shown. As can be seen, the cam assembly 28 includes a cam base 30 that is statically associated with the jaw 22. As used herein, "statically associated with" signifies that the cam base 30 is somehow associated with the jaw 22, by connection or otherwise, so that relative linear movement between the cam base 30 and jaw 22 does not occur during adjustment of the distance D1 between the jaws 22 and 24. The cam base 30 includes a ramped portion 50 that extends in at least two dimensions. As can be seen in FIG. 2, the ramped portion 50 can be between a first holding portion 52, shown as a flat portion, and a second holding portion 54, also shown as a flat portion. It should be appreciated that while the holding portions 52 and 54 are shown as being flat, it is contemplated that the holding portions 52 and 54 can also be curved or otherwise shaped, the significance of which will be described further herein. A pair of first bumps 56 can be formed on the first flat portion 52 and a pair of second bumps 58 can be formed on the second flat portion 54, the significance of which will also be described further herein. The bumps 56 and 58 can each have a bump height H1 and H2 relative to their respective flat portions 52 and 54, which can be adjusted as desired. The cam base 30 has a perimeter 60 defining outer edges of the cam base 30. The ramped portion 50 can extend away from the first flat portion 52 as the ramped portion 50 approaches the perimeter 60 until reaching the second flat portion 54, which can define a portion of the perimeter 60 and the end of the ramped portion 50.

The cam assembly 28 further includes a cam lever 32 pivotally connected to the ledged portion 46 of the connector 26 by a pivot pin 51, which defines an axis of rotation A1. The cam lever 32 can pivot about the axis of rotation A1, which will be further described herein. The cam lever 32 can include a cam portion 62 that is held against the cam base 30 and a lever portion 64 connected to the cam portion 62. The cam portion 62 can have a connection feature 66, shown as a pivot pin opening, formed therein that the pivot pin 51 is held within to pivotally connect the cam lever 32 to the ledged portion 46 of the connector 26. It should be appreciated that while the connection feature 66 is shown as an opening, the connection feature 66 can be any type of feature that allows the cam lever 32 to be pivotally connected to the connector 26 such that the cam lever 32 can pivot about an axis of rotation defined by a connection formed between the connection feature 66 and another element, such as pivot pin 51. Alternatively, the connection feature 66 can itself define an axis of rotation that the cam lever 32 can pivot about when held against the cam base 30. The cam portion 62 defines a profile 68 on a peripheral surface that has varying widths along a cam length L1 of the cam portion 62. As can be seen, the profile 68 includes several reliefs 70, 72, 74 formed therein. As the cam lever 32 pivots about the axis of rotation A1, various parts of the profile 68 of the cam portion 62 contact the cam base 30. As the various locations of the profile 68 contact the cam base 30, the linear position of the connection feature 66 changes, relative to the cam base 30, based upon the increased or decreased width of the cam portion 62 at the varying locations on the profile 68. This can be seen illustrated in FIGS. 1-6 and will be further described herein.

Referring once again to FIG. 1, it can be seen that lever portion 64 of the cam lever 32 has a first end 76 connected to the cam portion 62 and a second end 78 opposite the first end 76. Put another way, the second end 78 can define a lever arm of the cam lever 32 relative to the connection feature 66. As can be seen in FIGS. 1-2, the cam lever 32 can be oriented such that an end axis A2 defined through the second end 78 of the lever portion 64 is orthogonal relative to the axis of rotation A1 and a flattened portion 80 of the cam portion 62 is held against the first flat portion 52. In this orientation, the jaws 22 and 24 have a maximum distance D1 formed therebetween due to the profile 68 of the cam portion 62 being held against the first flat portion 52 such that the connection feature 66, which is connected to the connector 26, has a minimal feature separation distance FSD1 from the exterior surface 48 of the jaw 22 and the first flat portion 52. It can be further seen that when the flattened portion 80 of the cam portion 62 is held against the first flat portion 52, ledges 82 of the ledged portion 46 can be held against the second flat portion 54. In this position, which can be referred to as a large sliding position, the jaws 22 and 24 are separated sufficiently to allow a relatively large diameter device, such as drill sleeve 300, to be inserted and slide in the holding recesses 34.

Figure 3:
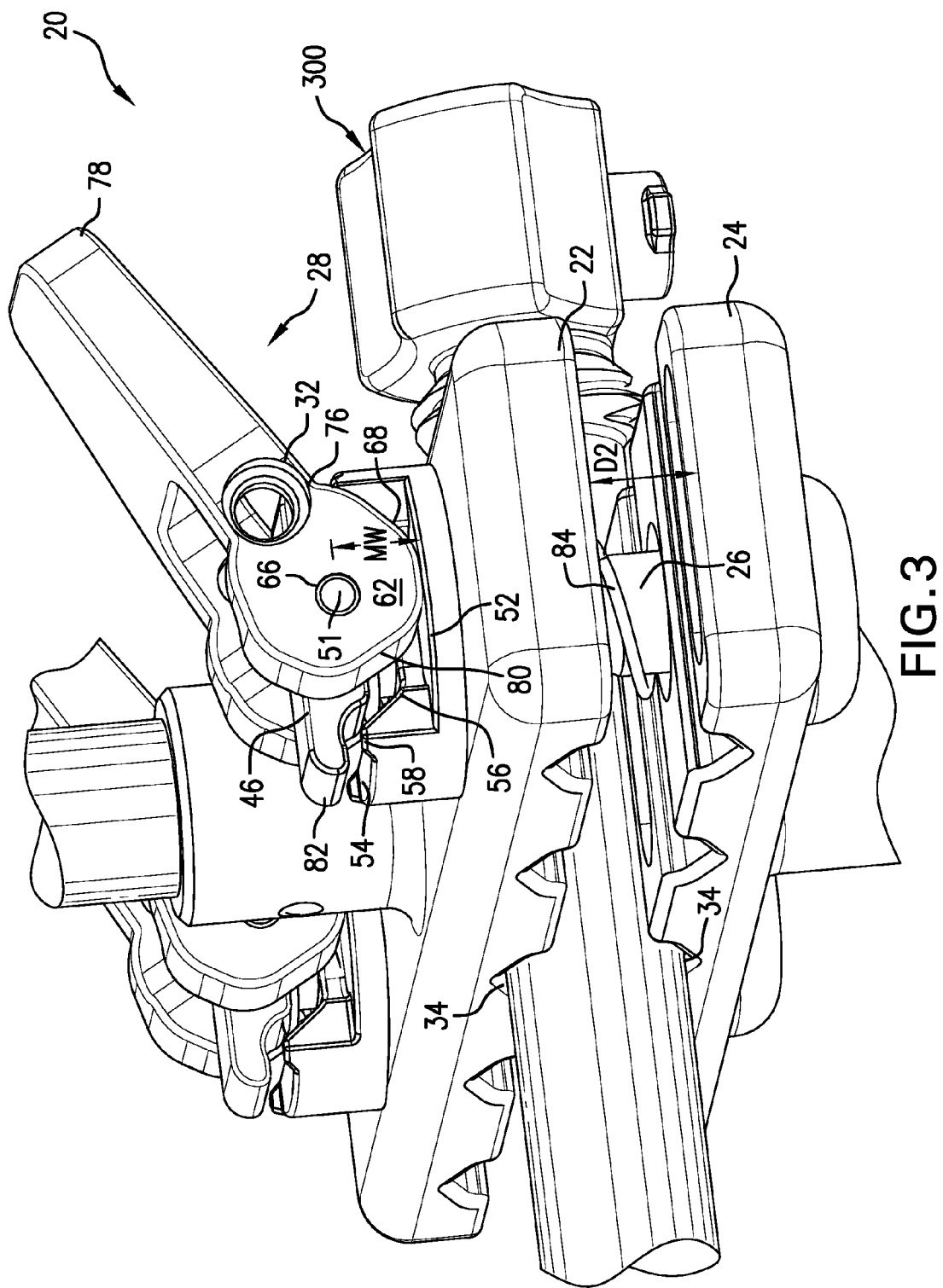
FIG. 3 is a perspective view of the tool cluster clamp shown in FIG. 1 with the cam assembly shown in a second position.

Referring now to FIG. 3, it can be seen that the cam lever 32 has been pivoted about the pivot pin 51 defining axis of rotation A1 toward the cam base 30 so that a different part of the profile 68 of the cam portion 62 is held against the first flat portion 52. As can be seen, the change in the part of the profile 68 held against the first flat portion 52 causes the connection feature 66, which is connected to the connector 26, to be separated further from the first flat portion 52 and raise the ledged portion 46 of the connector 26 relative to the first flat portion 52 as well. Since the ledged portion 46 of the connector 26 is raised relative to the first flat portion 52, which is evidenced by the ledges 82 of the ledged portion 46 raising off the second flat portion 54, the jaw 24 that the abutting portion 42 presses against is brought closer to the jaw 22 that the cam base 30 is affixed to and the distance between the jaws 22 and 24 is reduced. This allows for the jaws 22 and 24 to have a large locking distance D2 therebetween and lock down on the drill sleeve 300 held in holding recesses 34 of the jaws 22 and 24. This position can therefore be referred to as a large locking position. It should be appreciated that the profile 68 of the cam portion 62 of the cam lever 32 can be adjusted so that pivoting the cam lever 32 about the axis of rotation A1 causes differing amounts of actuation of the connector 26, depending on the number of degrees the cam lever 32 is pivoted. For example, the profile 68 can be adjusted so that pivoting the cam lever 32 90 degrees or more about the axis of rotation A1 causes a maximum width MW1 of the cam portion 62 to be held against the first flat portion 52, giving the connection feature 66 and connector 26 maximum separation from the first flat portion 52 for when the cam lever 32 is held against the first flat portion 52. It can be further seen in FIG. 3 that a biasing member 84, shown as a tension spring, is connected to the connector 26 and forces both the connector 26 and the cam lever 32 toward the cam base 30. The ledged portion 46 of the connector 26 can be lifted off the cam base 30 due to the profile 68 of the cam portion 62, but the tension spring 84 can generally keep the cam lever 32, especially the cam portion 62, held against the cam base 30 to keep the cam assembly 28 together.

Figure 4:
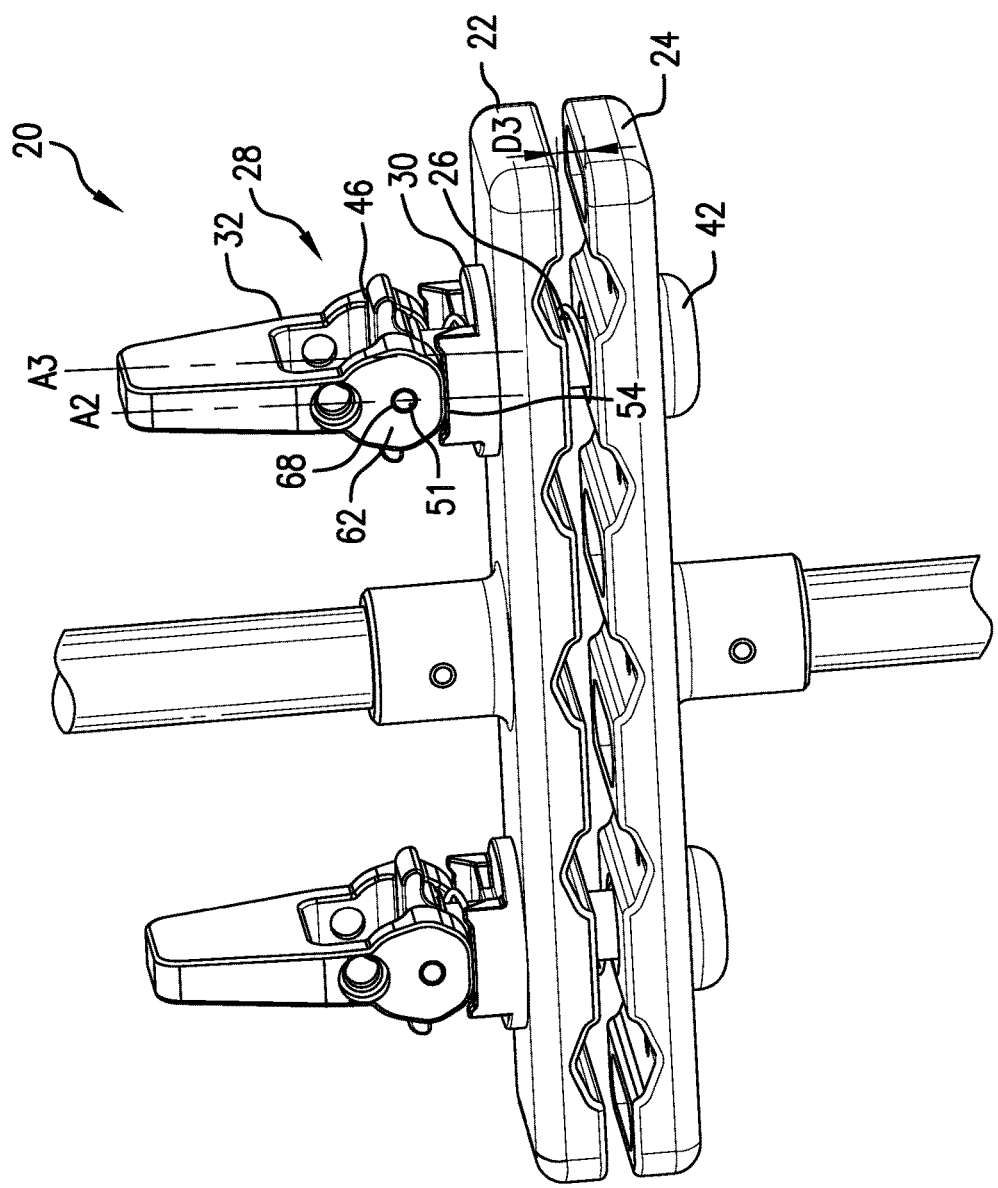
FIG. 4 is a perspective view of the tool cluster clamp shown in FIGS. 1 and 3 with the cam assembly shown in a third position.
Figure 5:
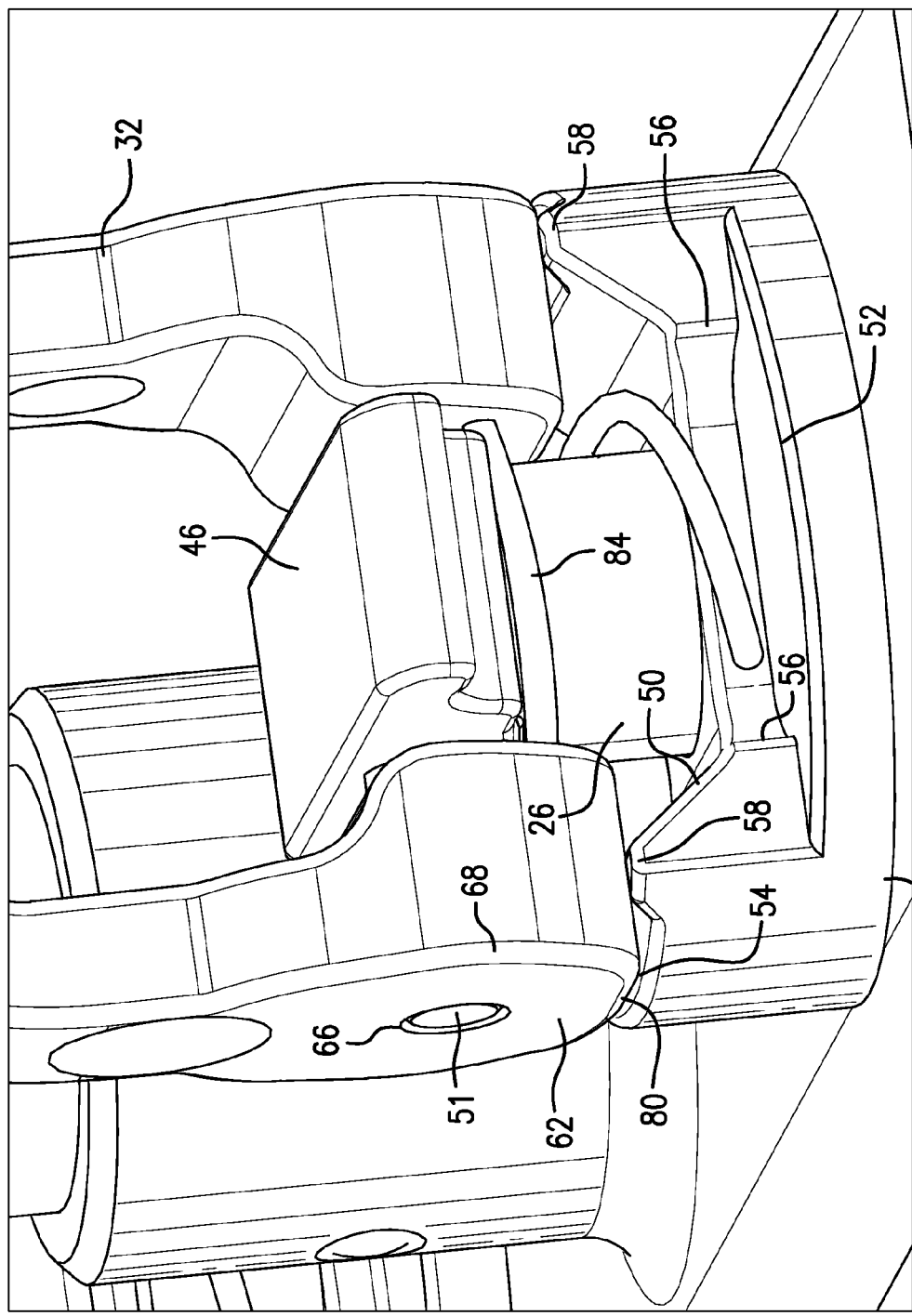
FIG. 5 is a perspective view of the cam assembly shown in FIG. 2 in the third position shown in FIG. 4.

Referring now to FIGS. 4-5, the tool cluster clamp 20 is shown with the cam lever 32 oriented in a small sliding position. As can be seen, a distance D3 is formed between the jaws 22 and 24 that is smaller than the distances D1 and D2 shown in FIGS. 1 and 3, respectively. This smaller distance is due to the cam lever 32 being rotated about a second axis of rotation A3 defined by the connector 26 along the ramped portion 50 of the cam base 30 so that the cam portion 62 of the cam lever 32 is held against the second flat portion 54. Since the ramped portion 50 extends away from the first flat portion 52, rotating the cam lever 32 along the ramped portion 50 to the second flat portion 54 causes the connection feature 66, and connected connector 26, to raise away from the first flat portion 52 and cause the abutting portion 42 of the connector 26 to force the jaw 24 closer to the other jaw 22. The cam base 30 can be formed so that the cam lever 32 is rotated 90 degrees about the second axis of rotation A3 along the ramped portion 50 to go from being held against the first flat portion 52 to being held against the second flat portion 54. It can therefore be seen that pivoting the cam lever 32 about the axis of rotation A1 defined by the pivot pin 51 and rotating the cam lever 32 about the second axis of rotation A3 defined by the connector 26 along the ramped portion 50 can both cause actuation of the connector 26 to adjust the distance between the jaws 22 and 24. Pivoting and/or rotating the cam lever 32 can therefore adjust the distance between the jaws 22 and 24, as desired.

To prevent the cam lever 32 from spontaneously rotating along the ramped portion 50 between the first flat portion 52 and the second flat portion 54, the previously described first bumps 56 and second bumps 58 can provide interference to rotation so that the cam lever 32 must be rotated about the second axis of rotation A2 with sufficient force to overcome the bumps 56 and 58 and further rotate in the desired direction. When the connector 26 includes a ledged portion 46 that is held against the second flat portion 54 when the cam portion 62 is held against the first flat portion 52, the second bumps 58 can also provide rotational interference to the ledges 82 of the ledged portion 46 as the connector 26 rotates with the cam lever 32.

Figure 6:
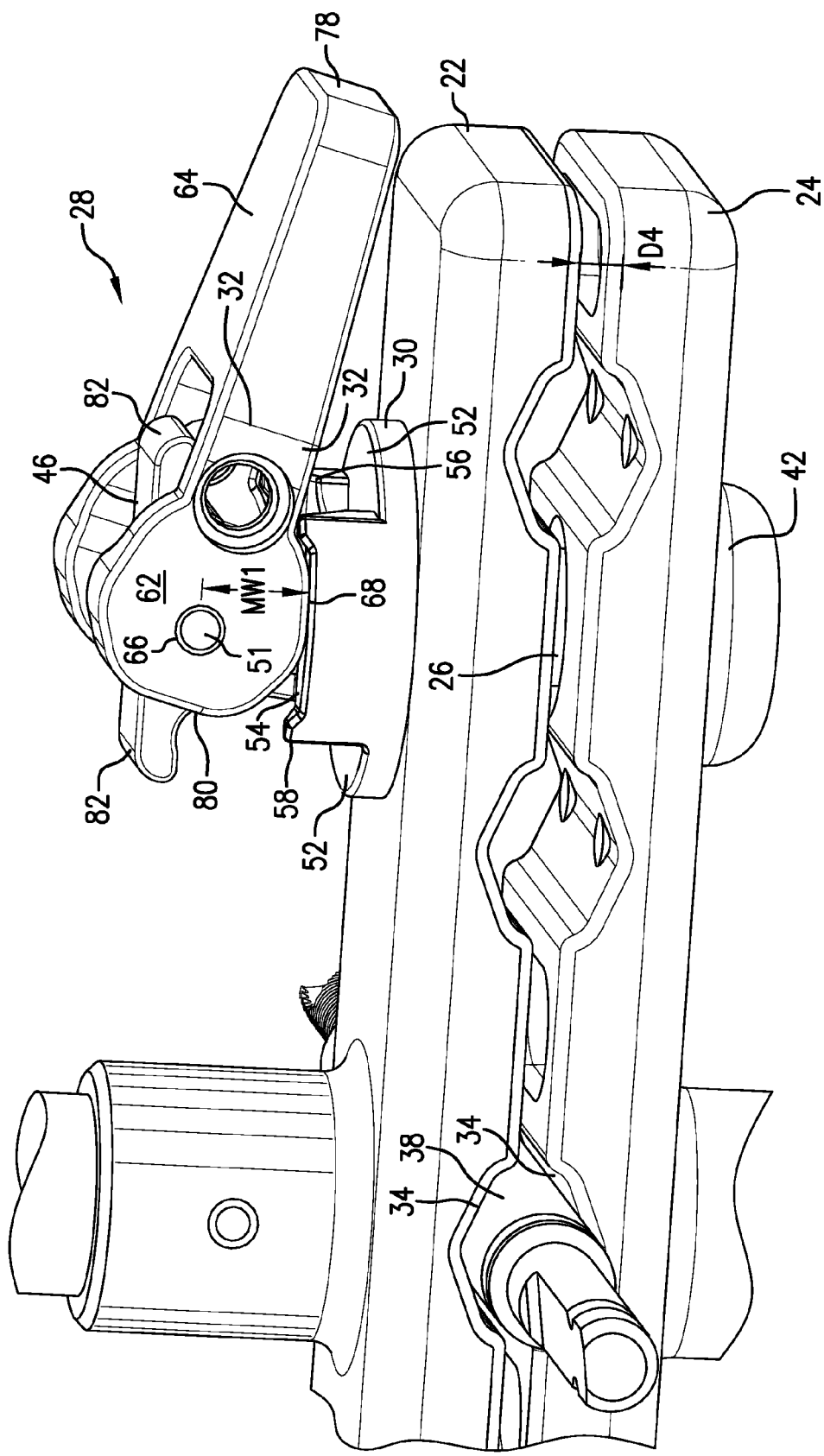
FIG. 6 is a perspective view of the tool cluster clamp shown in FIGS. 1 and 3-4 with the cam assembly shown in a fourth position.
Figure 7:
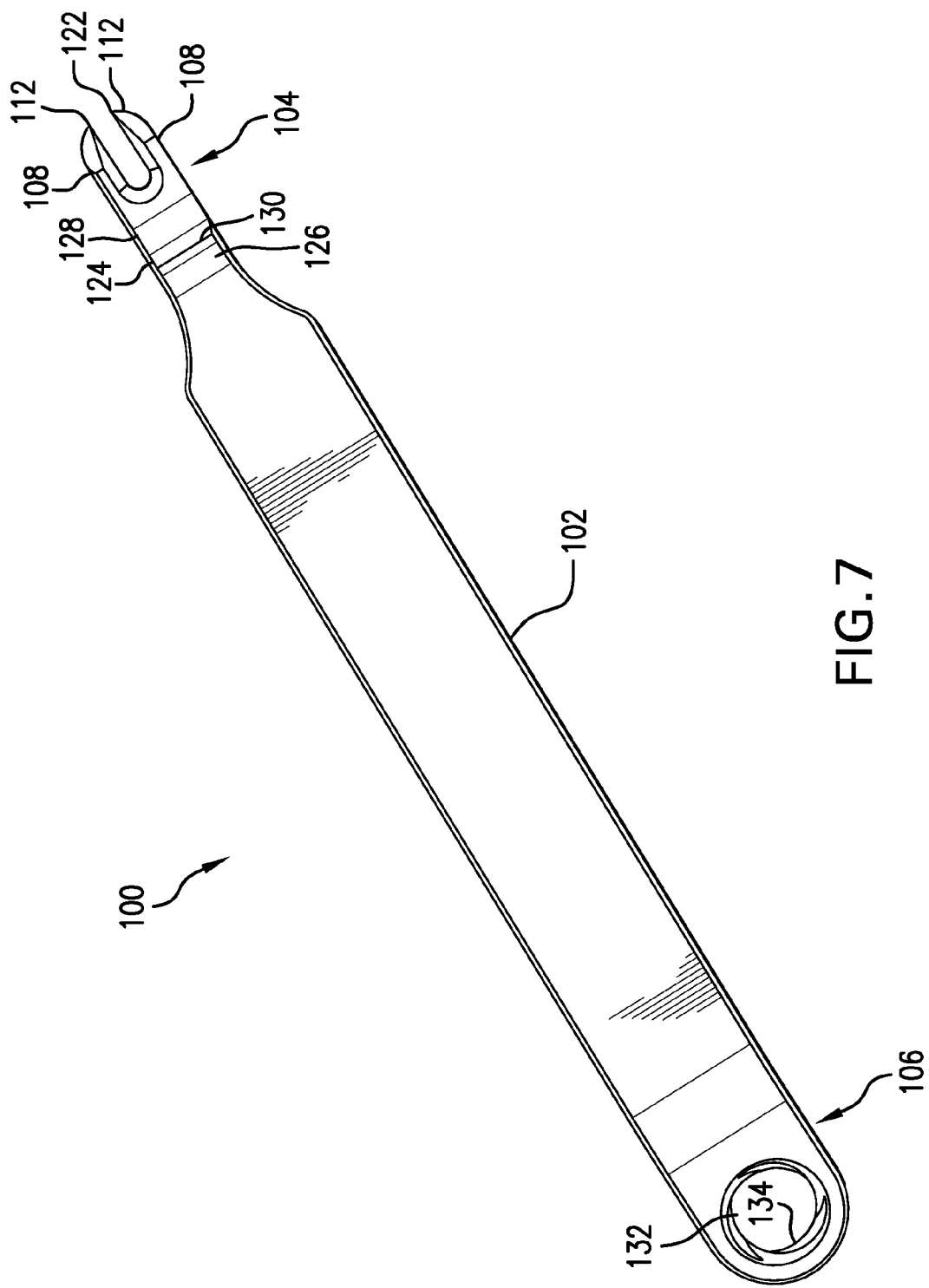
FIG. 7 is a perspective view of an embodiment of a tool that can be formed in accordance with the present invention.
Figure 8:
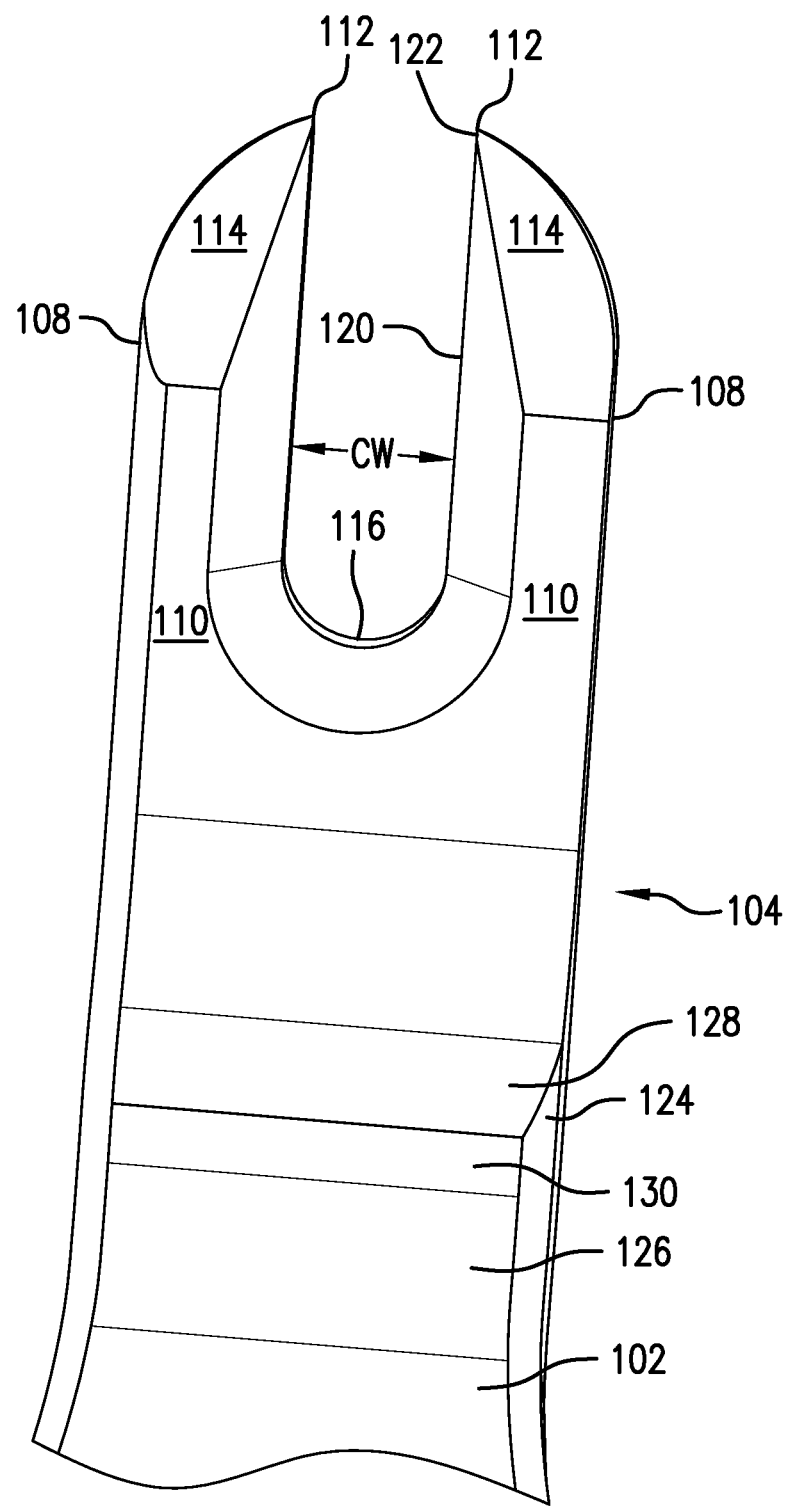
FIG. 8 is a perspective view of one end of the tool shown in FIG. 7.
Figure 9:
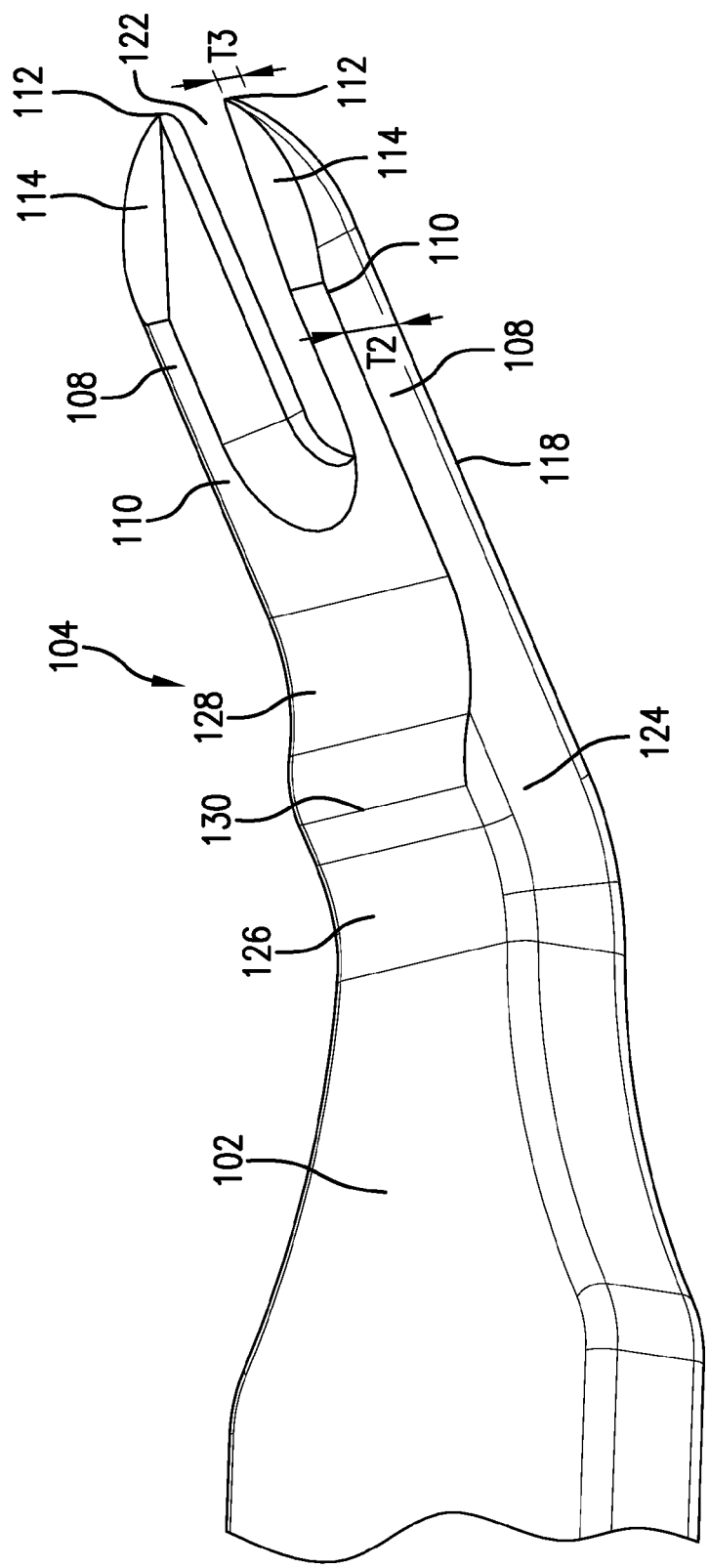
FIG. 9 is another perspective view of the end of the tool shown in FIG. 8.

As shown in FIG. 4, the cam lever 32 is oriented so that the end axis A2 is orthogonal to the axis of rotation A1 defined by the pivot pin 51. In this orientation, the jaws 22 and 24 are spaced so that a relatively small device, such as pin 38 shown in FIG. 6, can snugly slide within the holding recesses 34 of the jaws 22 and 24. Once the pin 38 is placed in the desired position within the holding recesses 34, the cam lever 32 can be pivoted about the axis of rotation A1 toward the cam base 30, as shown in FIG. 6, to force the abutting portion 42 of the connector 26 against the jaw 24 and decrease the separation between the jaws 22 and 24 to a small locking distance D4 and lock the pin 38 between the jaws 22 and 24. In the orientation of the cam lever 32 shown in FIG. 6, which can be referred to as the small locking position, the maximum width MW1 of the cam portion 62 is held against the second flat portion 54 to raise the connection feature 66 and connected connector 26 as far away from the first flat portion 52 as the profile 68 of the cam lever 32 allows while still being stable and held against the cam base 30. It is contemplated that the maximum width MW1 of the cam portion 62 can be held against one of the second bumps 58 to raise the connection feature 66 and connector 26 farther away from the first flat portion 52, but such a positioning might be unstable. Therefore, the small locking distance D4, shown when the cam lever 32 is in the small locking position, can be considered the minimum stable distance between the jaws 22 and 24. It should be appreciated that when the cam lever 32 is in the small locking position, the connection feature 66 and the first flat portion 52 have a maximum feature separation distance FSD2 formed therebetween, which corresponds with the small locking distance D4.

Referring now to FIGS. 7-10, an embodiment of a multiple use tool 100 according to the present invention is shown that generally includes a gripping portion 102, a first utility end 104 connected to the gripping portion 102, and a second utility end 106 opposite the first utility end 104 and connected to the gripping portion 102. As can be seen, the gripping portion 102 can have a substantially rectangular cross-section as shown, or other shapes that allow for a user to ergonomically grip and hold the tool 100 during use.

Referring specifically now to FIGS. 8-9 and 11-12, the first utility end 104 of the tool 100 is shown in greater detail. As can be seen, the first utility end 104 can include a pair of prongs 108 defining a space therebetween. Each prong 108 can have a top surface 110 defining a plane and a tip 112 with a curved surface 114 relative to the top surface 110. In this sense, the prongs 108 contour from the top surface 110 to the tips 112. The prongs 108 can be formed so that they share an interior surface 116 extending between the tips 112 of the two prongs 108. The interior surface 116 can be curved, as desired, or otherwise shaped to grip various objects between the prongs. The prongs 108 can have a prong thickness T2 defined between the top surface 110 of the prongs 108 and an opposing bottom surface 118 of the prongs 108. The thickness T2 of the prongs 108 can be constant throughout except for the countouring toward the tips 112, where the thickness T2 of the prongs 108 can decrease to a minimum prong thickness T3 at the tips 112. The space between the prongs 108 can define a channel 120 with a length that extends from an opening 122 between the prongs 108 to material of the prongs 108. Along the length of the channel 120, a channel width CW is defined between the prongs 108. The channel width CW, and channel 120 shape, can be constant along the bottom surface 118 of the prongs 108. However, between the bottom surface 118 and the top surface 110, the channel 120 shape and width CW can change due to the curvature of the interior surface 116. This allows the prongs 108 to grasp objects with similarly sized small sections connected to large sections that can greatly vary in size, such as pins.

A prong ramp 124 can be formed between the prongs 108 and the gripping portion 102 with a first ramp 126 adjacent to the gripping portion 102 and a second ramp 128 adjacent to the top surface 110 of the prongs 108. A median 130 can be formed between the first ramp 126 and second ramp 128 so that the first ramp 126 is formed concave relative to the median 130 and the second ramp 128 is partially concave to the median 130 before becoming convex.

Figure 10:
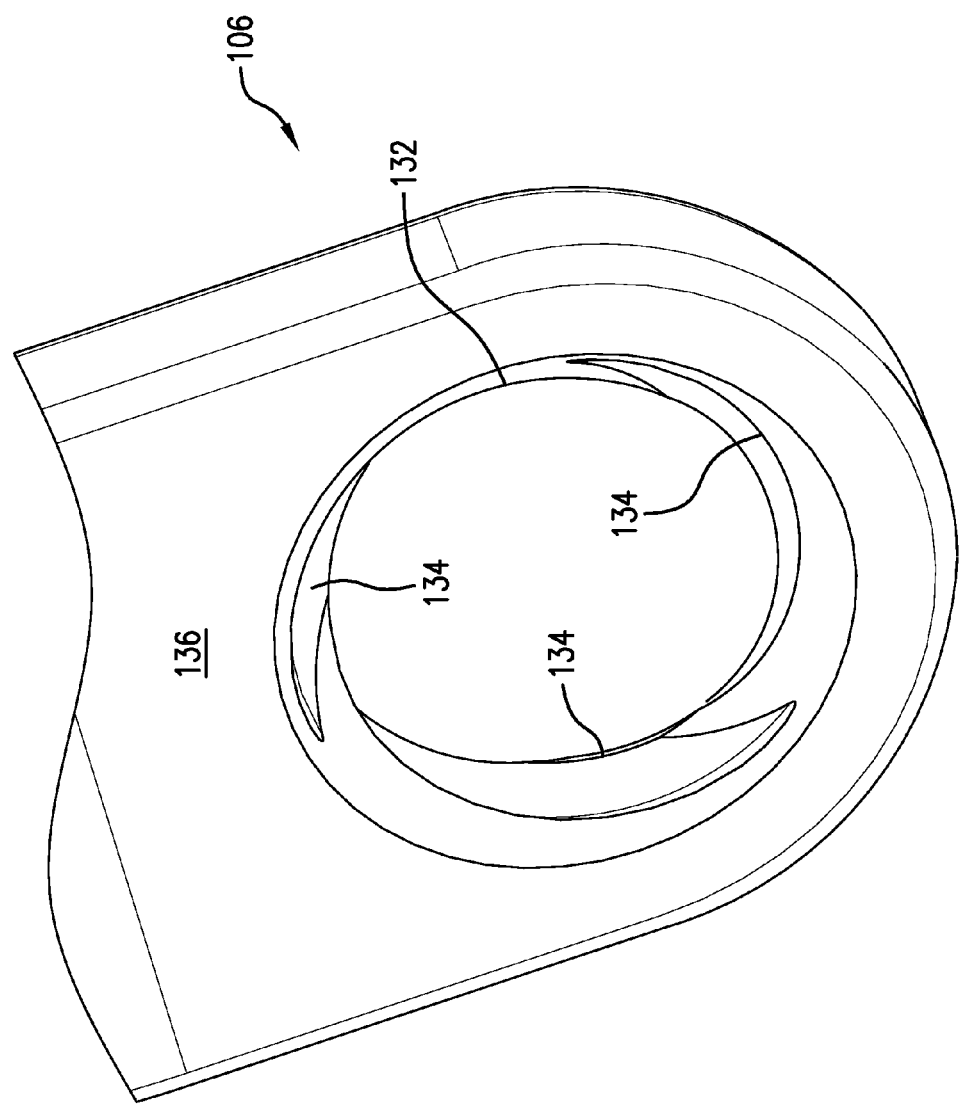
FIG. 10 is a perspective view of another end of the tool shown in FIG. 7 that is opposite the end shown in FIGS. 8-9.

Referring now to FIG. 10, the second utility end 106 is shown in greater detail. As can be seen, the second utility end 106 can include a drill sleeve opening 132 formed through that is shaped and sized to hold drill sleeves, such as drill sleeve 300 shown in FIG. 13. The drill sleeve opening 132 can have threading 134 formed in the walls thereof that the drill sleeve 300 or another tool can interact with to connect to the second utility end 106. As can be seen in FIGS. 7 and 11-13, the second utility end 106 can have a top surface 136 that is parallel to the top surface 110 of the prongs 108 but offset. The significance of this offset will be described further below.

Figure 11:
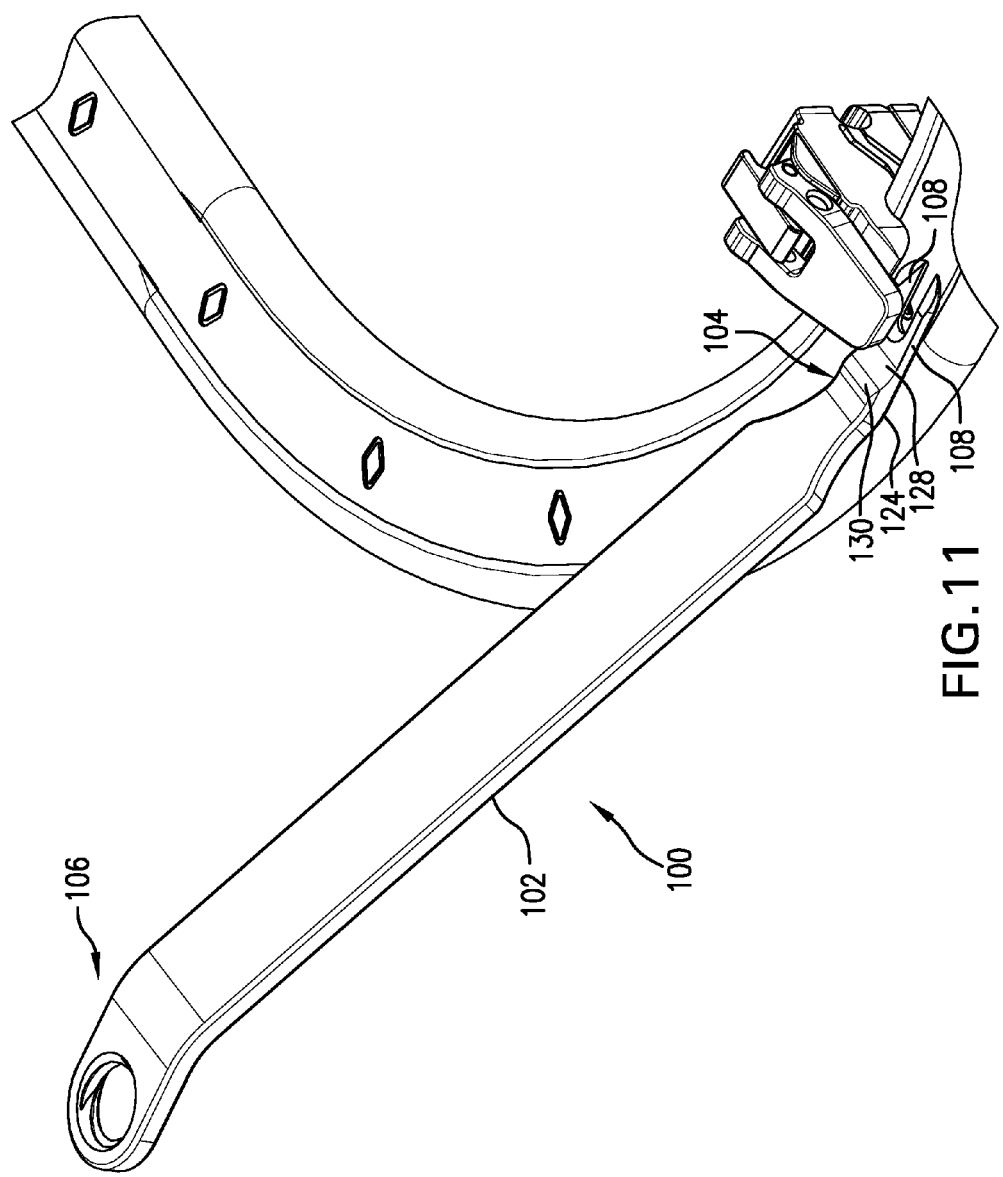
FIG. 11 is a perspective view of the tool shown in FIGS. 7-10 being wedged beneath a cam lever.
Figure 12:
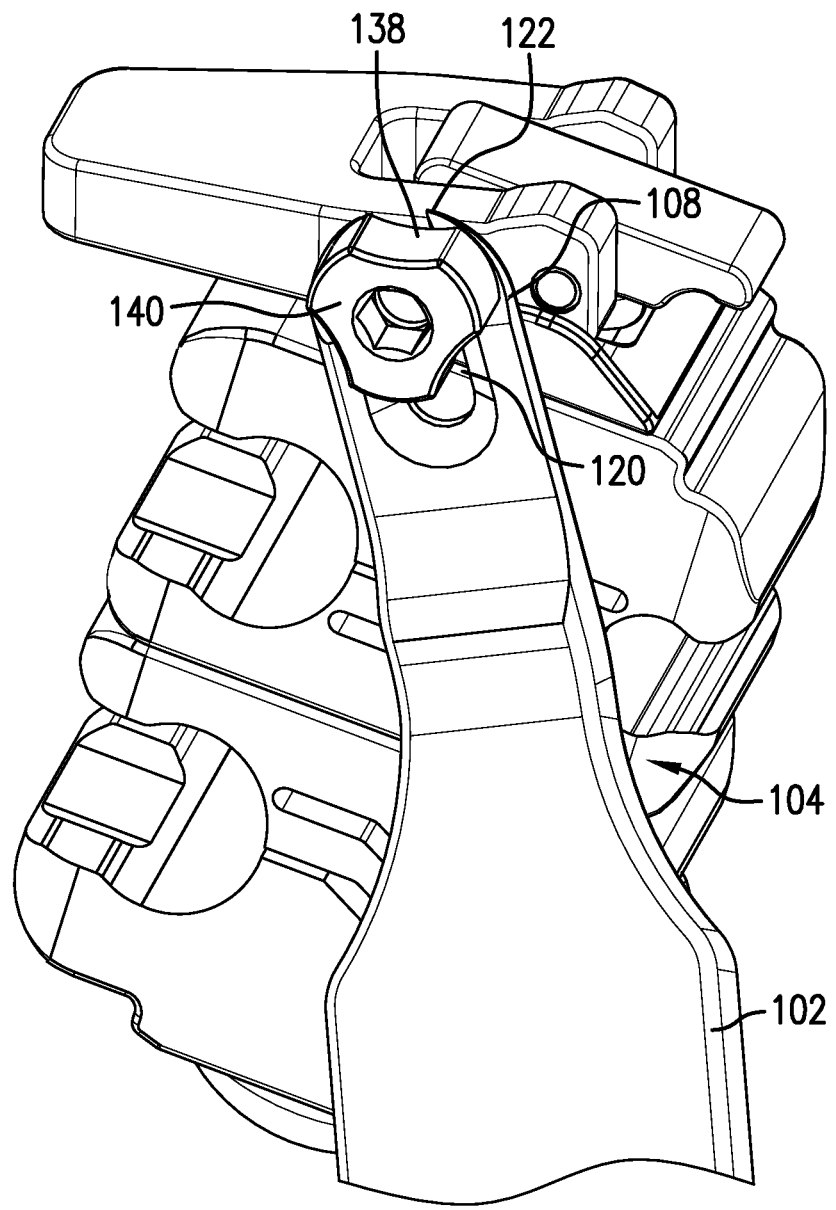
FIG. 12 is a perspective view of the tool shown in FIGS. 7-11 being used to grasp a pin.
Figure 13:
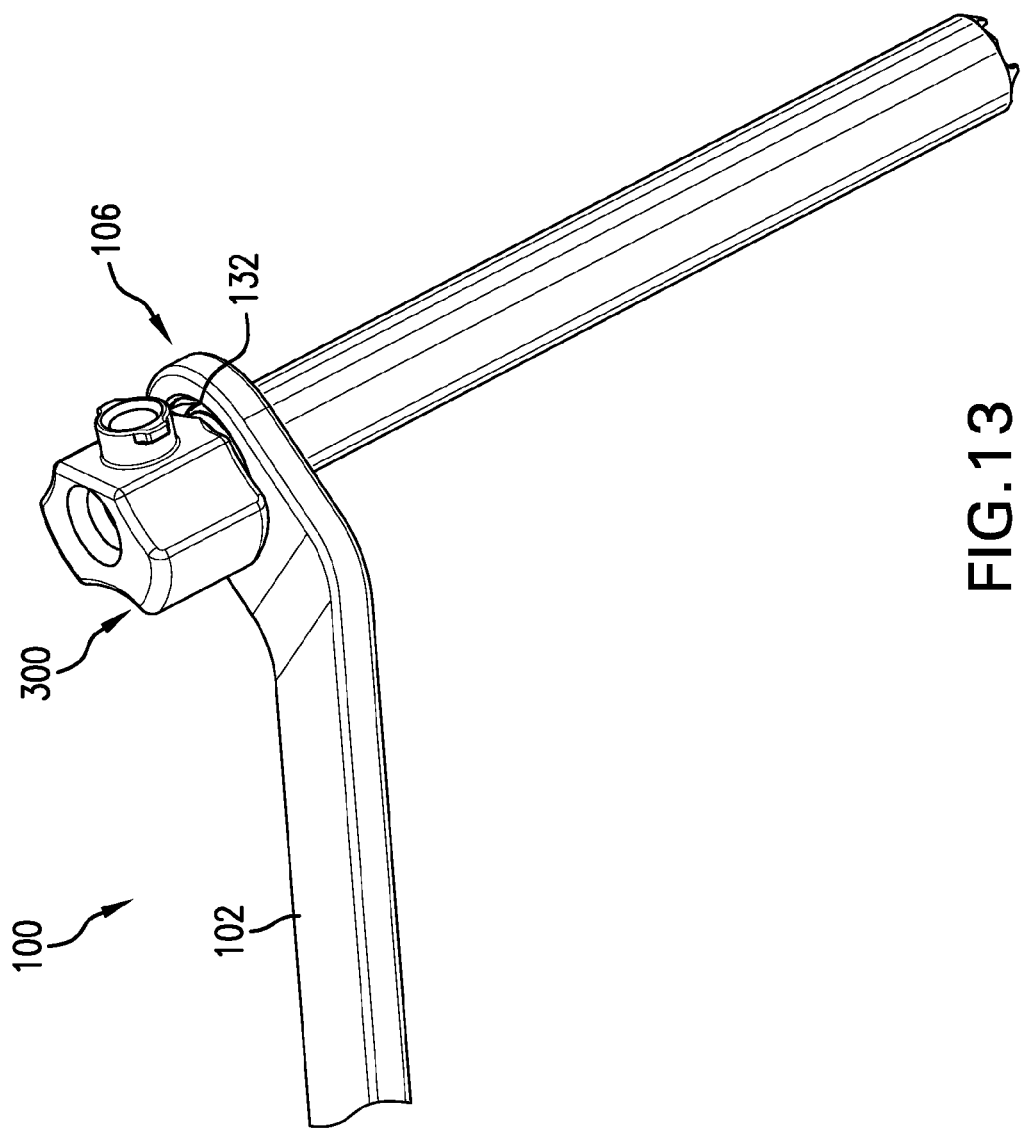
FIG. 13 is a perspective view of the tool shown in FIGS. 7-12 being used to grasp an embodiment of a drill sleeve formed according to the present invention.

Referring now to FIGS. 11-13, the tool 100 is shown being used for multiple purposes due to the geometry of its utility ends 104 and 106. As can be seen in FIG. 11, the prongs 108 of the first utility end 104 can be slid underneath a lever to assist a user in raising the lever. After the prongs 108 are slid under the lever so that the top surface 110 of the prongs 108 is contacting or in close proximity to the lever, the second utility end 106 can be forced in a direction opposite the opening direction of the lever to pry the lever. In this sense, the tool 100 can be used as a pry bar due to the offset between the first utility end 104 and second utility end 106 giving the user a mechanical advantage. Rather than prying the lever, the tool 100 can also be further slid under the lever so that the lever contacts the second ramp 128 and the tool 100 further raises the lever as the lever advances along the second ramp 128 toward the median 130. The raising of the lever due to its advancing along the second ramp 128 can be sufficient to loosen the lever sufficiently to unlock or to allow a user to get a grip of the lever and manually unlock the lever. Referring now to FIG. 12, the tool 100 is shown with a pin 138 being grasped in the channel 120 between the prongs 108. As the pin 138 advances through the opening 122 and toward the end of the channel 120, a pin head 140 of the pin 138 slides along the changing thickness of the tips 112 to help initially separate the pin 138. Once the pin 138 is advanced as far as it will go in the channel 120, the second utility end 106 can once again be pushed to pry the pin 138. Referring now to FIG. 13, the tool 100 is shown holding a drill sleeve 300 in the drill sleeve opening 132 of the second utility end 106. Once the drill sleeve 300 is fully advanced through the drill sleeve opening 132, the threading 134 can engage the drill sleeve 300 to give the tool 100 a better grip of the drill sleeve 300. It can therefore be seen that the tool 100 can be used in multiple useful ways.

Figure 14:
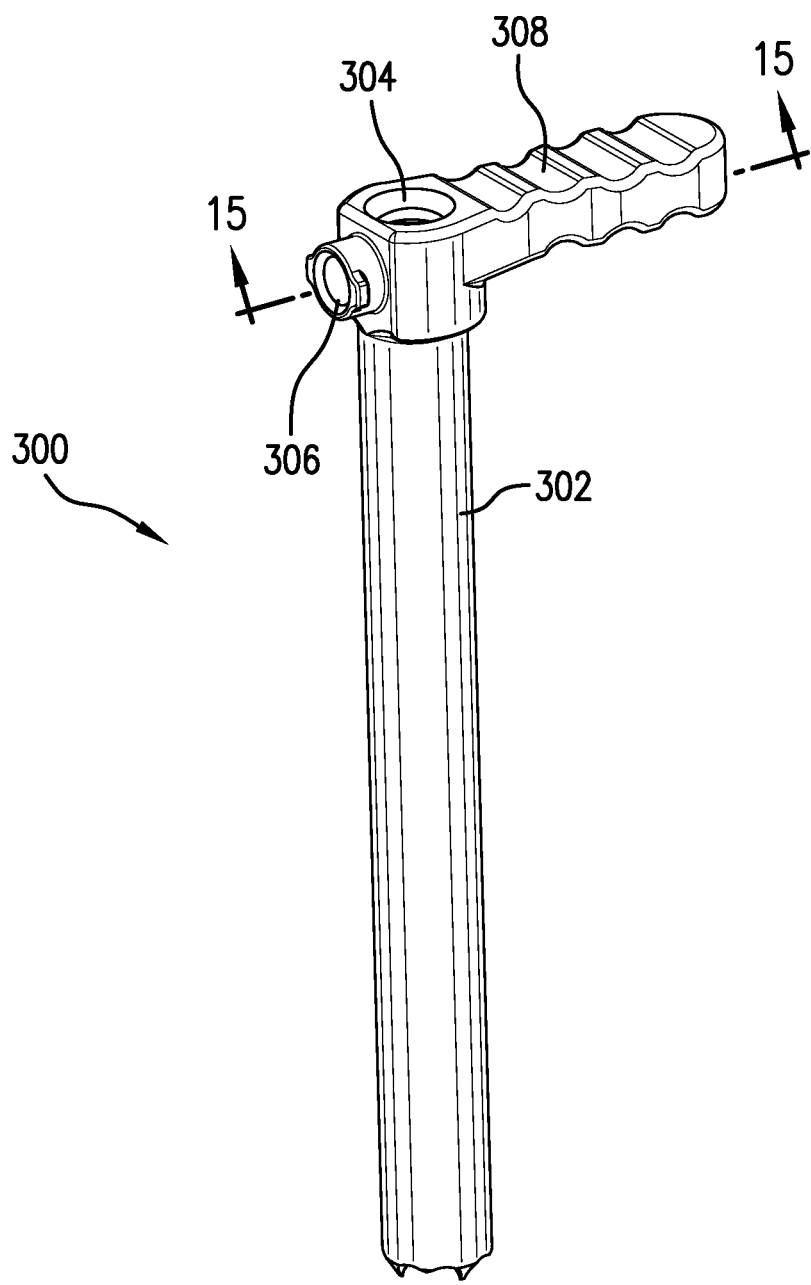
FIG. 14 is a perspective view of the drill sleeve shown in FIG. 13 apart from the tool.

Referring now to FIG. 14, an embodiment of a drill sleeve 300 formed according to the present invention is shown which generally includes a sleeve body 302 having a drill cavity 304 formed therethrough and a fluid inlet 306, shown as a luer lock, in fluid communication with the drill opening 304. While the fluid inlet 306 is shown as a luer lock, the fluid inlet 306 can be formed as any type of inlet that allows fluid, such as saline, to flow into the drill cavity 304. Optionally, a handle 308 can be attached to the sleeve body 302 to allow a user to hold on to the drill sleeve 300 during use.

Figure 15:
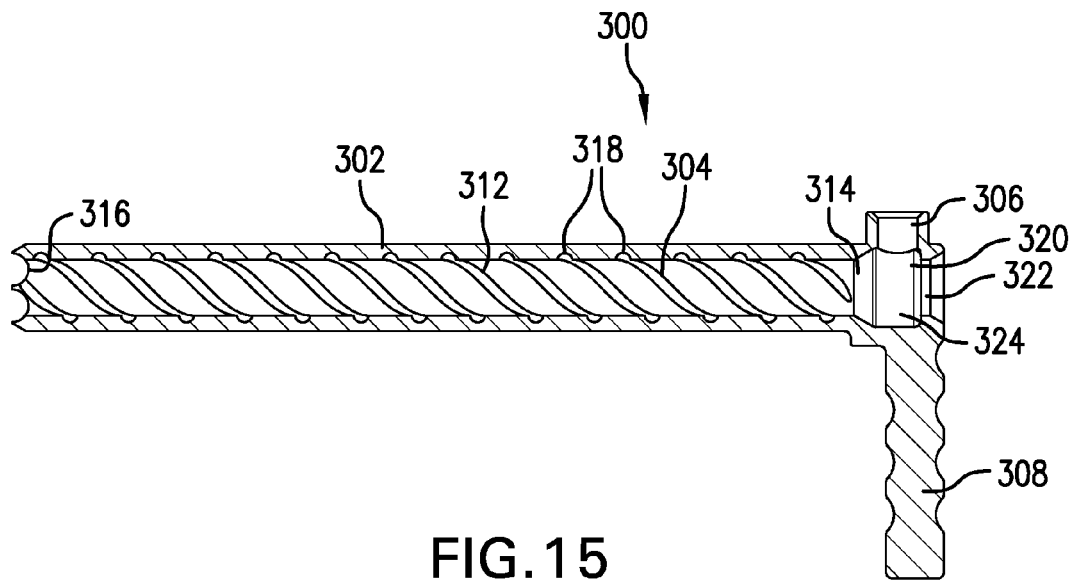
FIG. 15 is a cross-sectional view of the drill sleeve shown in FIG. 14 taken along line 14-14.
Figure 16:
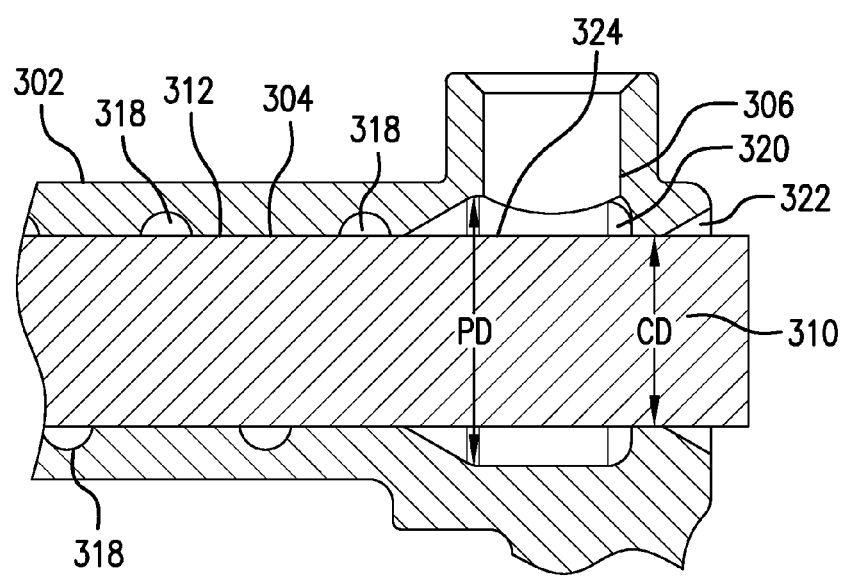
FIG. 16 is a cross-sectional view of the drill sleeve shown in FIGS. 13-15 with a drill held therein.

Referring now to FIGS. 15-16, a cross-sectional view of the drill sleeve 300 is shown. As can be seen in FIG. 16, when a drill 310 is placed inside the drill cavity 304, there is almost no clearance between an interior wall 312 of the sleeve body 302 defining the boundary of the drill cavity 304 and the drill 310. This is to ensure drilling accuracy as the drill 310 rotates. Due to the low amount of clearance between the drill 310 and the interior wall 312 of the sleeve body 302, there is little space for fluid flow between the drill 310 and the interior wall 312, which can severely restrict fluid flow from a proximal end 314 of the drill cavity 304 to a distal end 316 of the drill cavity 304. To assist in delivering fluid from the fluid inlet 306 to the distal end 316 of the drill cavity 304, one or more fluid channels 318 can be formed in the interior wall 312 of the sleeve body 302 that extend from a pooling zone 320, formed between the fluid inlet 306 and a drill entrance 322 of the sleeve body 302, to the distal end 316 of the drill cavity 304. The pooling zone 320, as shown, can be formed as a portion of the sleeve body 302 with a pooling bore 324 that has a pooling diameter PD greater than a cavity diameter CD of the drill cavity 304. The diameter of the drill entrance 322 can be the same as the cavity diameter CD or the pooling diameter PD, as desired. As shown in FIGS. 15-16, the fluid channel(s) 318 can be helically formed in the interior wall 312 of the sleeve body 302 so the fluid channel(s) 318 travel circumferentially down the interior wall 312 toward the distal end 316 of the drill cavity 304. When the drill cavity 304 is substantially filled by the drill 310, the fluid channel(s) 318 provide less restrictive fluid paths for fluid introduced into the fluid inlet 306 to flow through to reach the distal end 316 of the drill cavity 304. Since the pooling zone 320 fluidly connects to the fluid channel(s) 318 and the fluid inlet 306, fluid pressure can develop in the pooling zone 320, when the drill 310 is held in the drill cavity 304 and drill entrance 322, due to fluid being pushed through the fluid inlet 306 into the pooling zone 320. This developed fluid pressure can force fluid that is already in the pooling zone 320 into the fluid channel(s) 318, which provide a path of least resistance, so that fluid from the fluid inlet 306 consistently flows through the fluid channel(s) 318 to the distal end 316 of the drill cavity 304.

Figure 17:
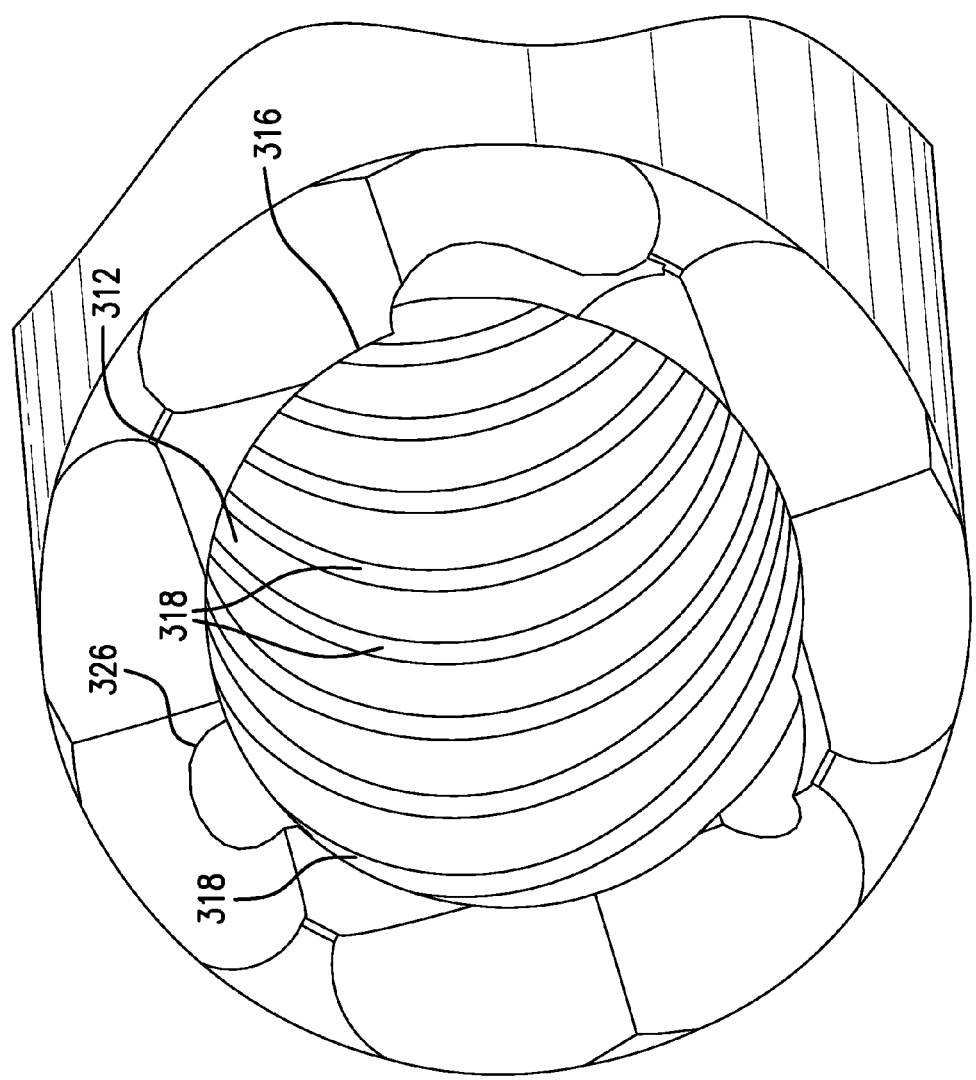
FIG. 17 is a perspective view of the drill sleeve shown in FIGS. 13-16.
Figure 18:
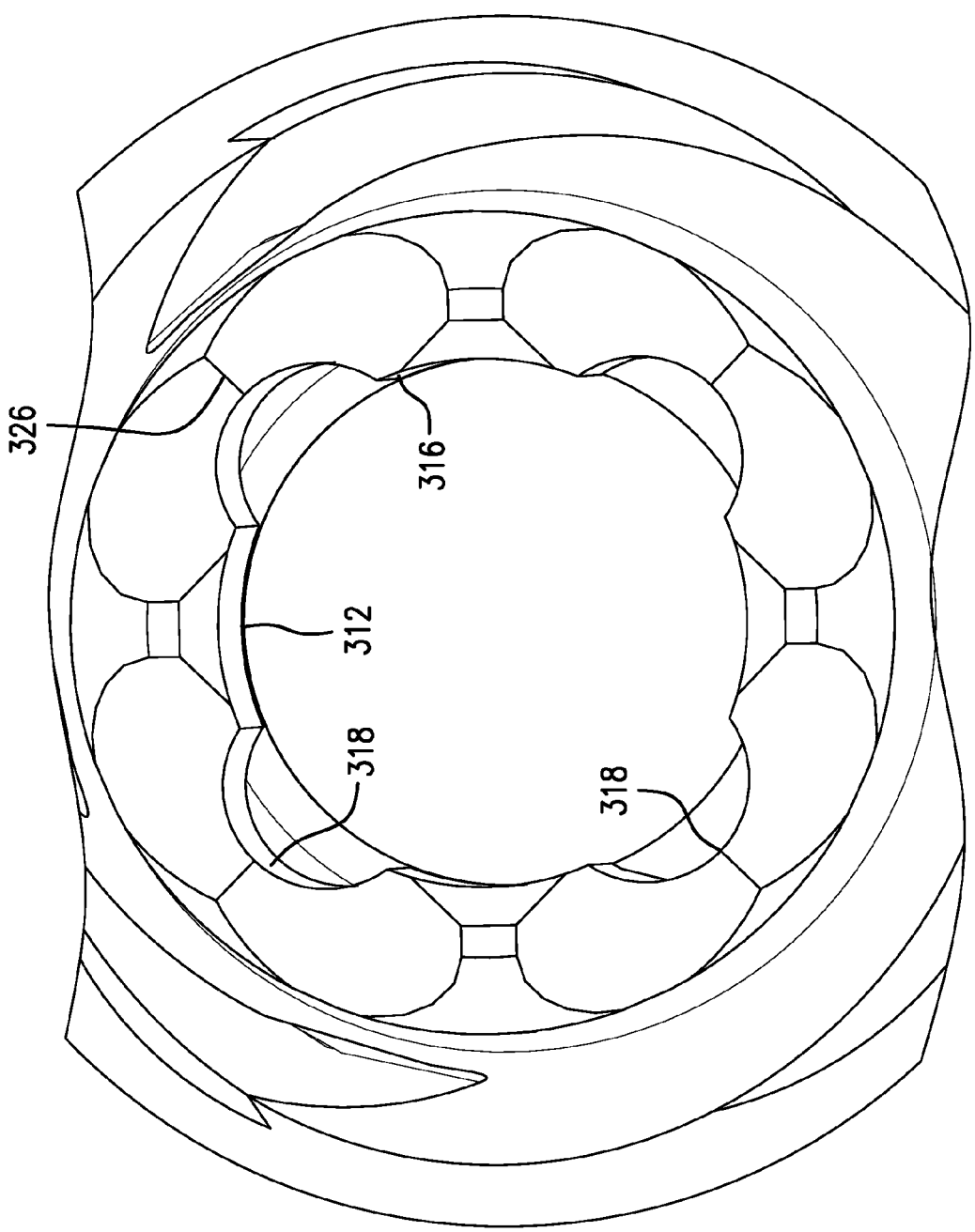
FIG. 18 is a perspective view of an embodiment of a drill sleeve formed according to the present invention that includes straight fluid channels.

Referring now to FIGS. 17-18, the distal end 316 of the drill cavity 304 is shown. As can be seen in, for example, FIG. 17, the fluid channels 318 connect to fluid outlets 326 formed in the sleeve body 302 at the distal end 316 of the drill cavity 304 so that fluid which has travelled through the fluid channels 318 can flow into the area in proximity to the distal end 316 of the drill cavity 304. That area could be, for example, a bone or other anatomic feature that the drill 310 is cutting through, with saline flowing through the fluid channels 318 to cool the drill 310 and cut bone tissue so that heat does not build up which could damage nearby healthy tissue. While helical fluid channels 318 are shown in FIGS. 15-17 as being formed in the interior wall 312, straight fluid channels 328 can also be formed in the interior wall 312 to the distal end 316 of the drill cavity 304, as shown in FIG. 18. It should therefore be appreciated that a variety of fluid channel shapes, sizes, and paths can be formed in the interior wall 312 to deliver fluid from the fluid inlet 306 to the distal end 316 of the drill cavity.

While this invention has been described with respect to at least one embodiment, the present invention can be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains and which fall within the limits of the appended claims.

What is claimed is:

1. An orthopaedic tool cluster clamp, comprising:
   a pair of jaws held together and defining a distance therebetween, one of said jaws being movable relative to one another to adjust said distance;
   a connector holding said jaws together, wherein actuation of said connector adjusts said distance between said jaws;
   a cam base including a ramped portion statically associated with one of said jaws; and
   a cam lever pivotally connected to said connector about an axis of rotation and held against said cam base, said cam lever defining a profile wherein rotating said cam lever along said ramped portion and pivoting said cam lever about said axis of rotation both cause actuation of said connector.

2. The clamp according to claim 1, wherein said cam base includes a first flat portion and a second flat portion, said ramped portion being between said first flat portion and said second flat portion.

3. The clamp according to claim 2, wherein said cam base includes a bump formed on at least one of said first flat portion and said second flat portion, said bump preventing free rotation of said cam lever along said ramped portion from at least one said first flat portion and said second flat portion.

4. The clamp according to claim 2, wherein said connector includes at least one ledge, said ledge being held against said second flat portion when said cam lever is held against said first flat portion.

5. The clamp according to claim 2, wherein said cam lever includes a cam portion and a lever portion connected to said cam portion, said cam portion being pivotally connected to said connector and held against said cam base, said lever portion having a first end connected to said cam portion and a second end opposite said first end.

6. The clamp according to claim 5, wherein said second end of said lever portion defines an end axis, said distance between said jaws being at a maximum when said end axis is orthogonal relative to said axis of rotation and said cam portion is held against said first flat portion.

7. The clamp according to claim 6, wherein said cam portion includes a flattened portion held against said first flat portion when said distance between said jaws is at said maximum.

8. The clamp according to claim 5, wherein said profile includes a plurality of reliefs formed therein.

9. The clamp according to claim 5, wherein said cam portion defines a maximum width, said distance between said jaws being at a minimum when said cam lever is positioned so that said maximum width is held against said second flat portion of said cam base.

10. The clamp according to claim 1, further comprising a biasing member forcing said cam lever against said cam base.

11. The clamp according to claim 1, wherein said connector defines a second axis of rotation, wherein rotation of said cam lever about said second axis of rotation along said ramped portion causes actuation of said connector.

12. The clamp according to claim 1, wherein said cam base includes at least two holding portions, said ramped portion being between said at least two holding portions.

13. The clamp according to claim 12, wherein said at least two holding portions include at least one flat portion.

14. A cam assembly, comprising:
    a cam base having a first flat portion, a second flat portion, a ramped portion positioned between said first and second flat portions, and a bump formed on at least one of said first and second flat portions; and
    a cam lever held against said cam base and having a connection feature defining an axis of rotation, said cam lever defining a profile wherein rotating said cam lever along said ramped portion and pivoting said cam lever about said axis of rotation both cause linear movement of said connection feature, said bump preventing free rotation of said cam lever along said ramped portion from at least one of said first and second flat portions.

15. The cam assembly according to claim 14, wherein said cam lever includes a cam portion and a lever portion connected to said cam portion, said cam portion being held against said cam base, said lever portion having a first end connected to said cam portion and a second end opposite said first end.

16. The cam assembly according to claim 15, wherein said profile includes a plurality of reliefs formed therein.

17. A cam assembly, comprising:
    a cam base a ramped portion; wherein said cam base includes a first flat portion and a second flat portion, said ramped portion being between said first flat portion and said second flat portion; and
    a cam lever held against said cam base and having a connection feature defining an axis of rotation, said cam lever defining a profile wherein rotating said cam lever along said ramped portion and pivoting said cam lever about said axis of rotation both cause linear movement of said connection feature;
    wherein said cam lever includes a cam portion and a lever portion connected to said cam portion, said cam portion being held against said cam base, said lever portion having a first end connected to said cam portion and a second end opposite said first end; and
    wherein said cam portion defines a maximum width and said connection feature and said first flat portion define a feature separation distance therebetween, said feature separation distance being at a maximum when said cam lever is positioned so that said maximum width is held against said second flat portion of said cam base.

18. The cam assembly according to claim 14, further comprising a biasing member forcing said cam lever against said cam base.

* * * * *